United States Patent
Daidoji et al.

(10) Patent No.: US 10,542,865 B2
(45) Date of Patent: Jan. 28, 2020

(54) ENDOSCOPIC SYSTEM WITH SPECKLE REDUCTION UNIT

(71) Applicant: OLYMPUS CORPORATION, Tokyo (JP)

(72) Inventors: Bakusui Daidoji, Hachioji (JP); Takeshi Ito, Hino (JP); Hiroyuki Kamee, Koganei (JP)

(73) Assignee: OLYMPUS CORPORATION, Tokyo (JP)

( * ) Notice: Subject to any disclaimer, the term of this patent is extended or adjusted under 35 U.S.C. 154(b) by 484 days.

(21) Appl. No.: 15/146,934

(22) Filed: May 5, 2016

(65) Prior Publication Data

US 2016/0242626 A1 Aug. 25, 2016

Related U.S. Application Data

(63) Continuation of application No. PCT/JP2014/071292, filed on Aug. 12, 2014.

(30) Foreign Application Priority Data

Nov. 13, 2013 (JP) .................................. 2013-235445

(51) Int. Cl.
*A61B 1/00* (2006.01)
*A61B 1/04* (2006.01)
(Continued)

(52) U.S. Cl.
CPC ...... *A61B 1/00009* (2013.01); *A61B 1/00006* (2013.01); *A61B 1/00039* (2013.01);
(Continued)

(58) Field of Classification Search
CPC ............ A61B 1/00009; A61B 1/00006; A61B 1/00039; A61B 1/00045; A61B 1/00096;
(Continued)

(56) References Cited

U.S. PATENT DOCUMENTS 5,956,447 A * 9/1999 Zel'Dovich .............. G02B 6/02
 235/462.01
6,993,167 B1 * 1/2006 Skladnev ............. A61B 5/0059
 382/128

(Continued)

FOREIGN PATENT DOCUMENTS

EP 2 399 508 A1 12/2011
JP 2004-512538 A 4/2004
(Continued)

OTHER PUBLICATIONS

International Search Report dated Nov. 18, 2014 issued in PCT/JP2014/071292.

(Continued)

*Primary Examiner* — Timothy J Neal
*Assistant Examiner* — William B Chou
(74) *Attorney, Agent, or Firm* — Scully, Scott, Murphy & Presser, P.C.

(57) ABSTRACT

An endoscopic system includes a speckle reduction unit which is reduce speckle generated on an observed portion by light that has coherence, a controller which controls an operation of the speckle reduction unit and a plurality of observation modes including a speckle observation mode of observing the observed portion based on the speckle generated on the observed portion by the light. The controller controls the operation of the speckle reduction unit in accordance with the observation modes such that the speckle reduction unit does not reduce the speckle in the speckle observation mode and the speckle reduction unit reduces the speckle in the observation modes other than the speckle observation mode.

12 Claims, 8 Drawing Sheets

(51) Int. Cl.
*A61B 1/06* (2006.01)
*A61B 5/00* (2006.01)

(52) U.S. Cl.
CPC ...... *A61B 1/00045* (2013.01); *A61B 1/00096* (2013.01); *A61B 1/04* (2013.01); *A61B 1/0638* (2013.01); *A61B 5/0066* (2013.01)

(58) Field of Classification Search
CPC ..... A61B 1/00163; A61B 1/04; A61B 1/0638; A61B 1/07; A61B 5/0066; G02B 23/2453; G02B 27/48
USPC ....... 600/108, 109, 113, 153, 160, 166, 167, 600/168, 170, 171, 172, 173, 175, 176, 600/177, 178, 180, 181
See application file for complete search history.

(56) References Cited

U.S. PATENT DOCUMENTS

| | | | | |
|---|---|---|---|---|
| 8,097,864 | B2* | 1/2012 | Tearney | G01N 21/6458 250/459.1 |
| 2002/0183601 | A1 | 12/2002 | Tearney et al. | |
| 2003/0120156 | A1 | 6/2003 | Forrester et al. | |
| 2006/0013544 | A1* | 1/2006 | Bouma | G02B 6/02042 385/116 |
| 2008/0097225 | A1* | 4/2008 | Tearney | A61B 18/22 600/478 |
| 2008/0146929 | A1* | 6/2008 | Satoh | A61B 8/08 600/443 |
| 2010/0121190 | A1* | 5/2010 | Pagoulatos | A61B 8/00 600/437 |
| 2010/0210910 | A1* | 8/2010 | Shimotsu | G02B 6/04 600/178 |
| 2010/0268034 | A1* | 10/2010 | Krattiger | A61B 1/00165 600/178 |
| 2010/0280315 | A1* | 11/2010 | Pan | A61B 5/0066 600/109 |
| 2011/0319712 | A1 | 12/2011 | Kuroda et al. | |
| 2012/0116157 | A1* | 5/2012 | Seto | A61B 1/00057 600/109 |
| 2012/0190928 | A1* | 7/2012 | Boudoux | A61B 1/0017 600/166 |

FOREIGN PATENT DOCUMENTS

| | | |
|---|---|---|
| JP | 2009-240560 A | 10/2009 |
| JP | 2010-172651 A | 8/2010 |
| JP | 2011-130902 A | 7/2011 |
| WO | WO 02/36015 A1 | 5/2002 |

OTHER PUBLICATIONS

Bray, R.C. et al., "Endoscopic Laser Speckle Imaging of Tissue Blood Flow: Applications in the Human Knee", Journal of Orthopaedic Research, vol. 24, No. 8, Aug. 1, 2006, pp. 1650-1659.
Extended Supplementary European Search Report dated Jul. 28, 2017 in European Patent Application No. 14 86 1726.9.
Chinese Office Action dated Nov. 15, 2017 in Chinese Patent Application No. 201480061249.1.
English translation of International Preliminary Report on Patentability dated May 26, 2016 together with the Written Opinion received in related International Application No. PCT/JP2014/071292.

* cited by examiner

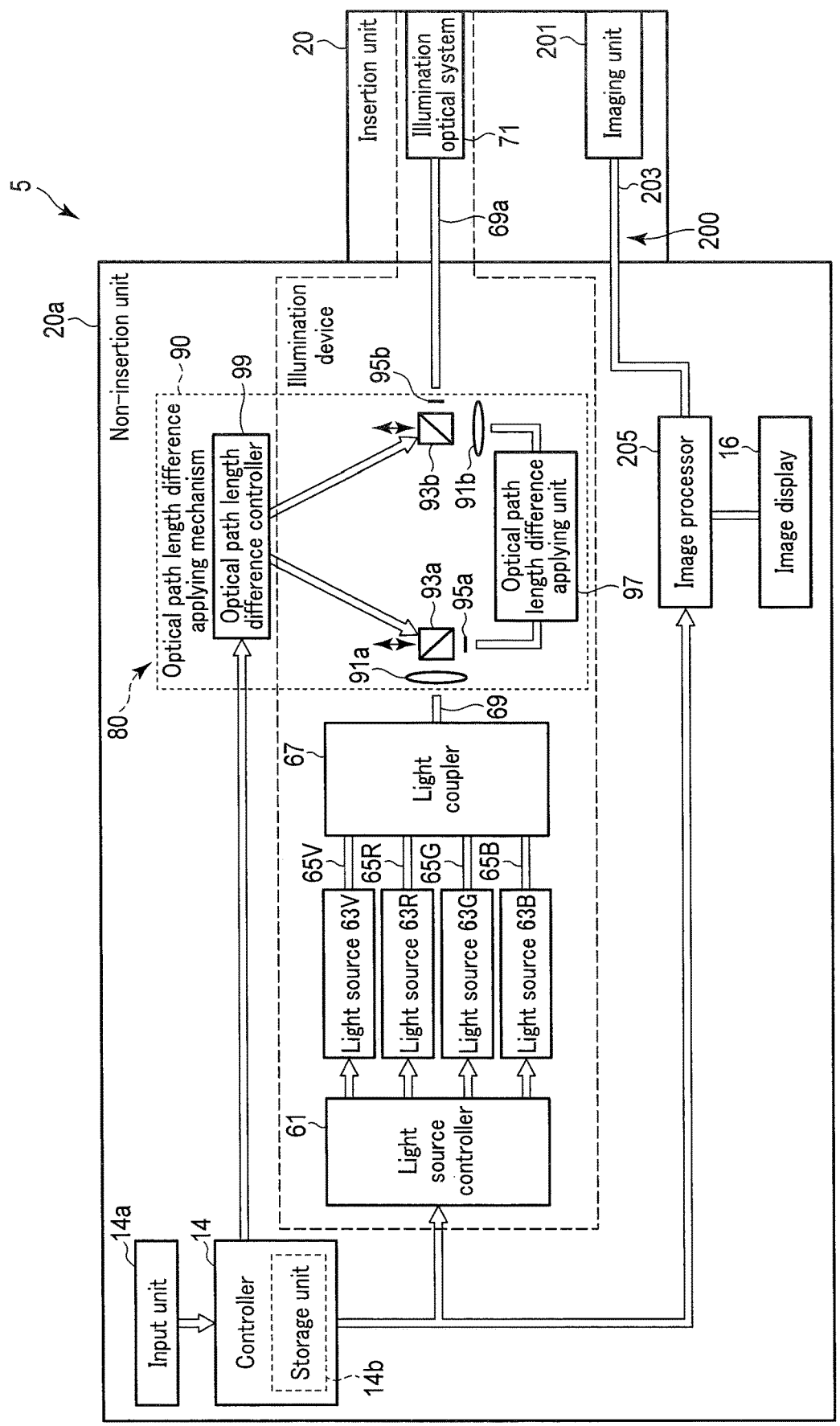
F I G. 3A

ENDOSCOPIC SYSTEM WITH SPECKLE REDUCTION UNIT

CROSS-REFERENCE TO RELATED APPLICATIONS

This application is a Continuation application of PCT Application No. PCT/JP2014/071292, filed Aug. 12, 2014 and based upon and claiming the benefit of priority from prior Japanese Patent Application No. 2013-235445, filed Nov. 13, 2013, the entire contents of all of which are incorporated herein by reference.

BACKGROUND OF THE INVENTION

1. Field of the Invention

The present invention relates to an endoscopic system including an endoscope.

2. Description of the Related Art

In recent years, development of optical probes utilizing characteristics of laser light has taken place. Such optical probes analyze tissues based on speckle generated when laser light is applied to the tissues. For example, Jpn. PCT. National Publication No. 2004-512538 is mentioned as a disclosure of the analyzing method. The optical probes are assumed to be used together with, for example, an endoscope.

BRIEF SUMMARY OF THE INVENTION

In an aspect of an endoscopic system of the present invention which an observed portion is observed by using light that has coherence, the aspect includes a speckle reduction unit which is reduce speckle generated on the observed portion by the light that has the coherence; a controller which controls an operation of the speckle reduction unit; and a plurality of observation modes including a speckle observation mode of observing the observed portion based on the speckle generated on the observed portion by the light, wherein the controller controls the operation of the speckle reduction unit in accordance with the observation modes such that the speckle reduction unit does not reduce the speckle in the speckle observation mode and the speckle reduction unit reduces the speckle in the observation modes other than the speckle observation mode.

Advantages of the invention will be set forth in the description which follows, and in part will be obvious from the description, or may be learned by practice of the invention. Advantages of the invention may be realized and obtained by means of the instrumentalities and combinations particularly pointed out hereinafter.

BRIEF DESCRIPTION OF THE SEVERAL VIEWS OF THE DRAWING

The accompanying drawings, which are incorporated in and constitute apart of the specification, illustrate embodiments of the invention, and together with the general description given above and the detailed description of the embodiments given below, serve to explain the principles of the invention.

FIG. 3A is a schematic diagram of an endoscopic system according to a third embodiment;

DETAILED DESCRIPTION OF THE INVENTION

Embodiments of the present invention will be explained in detail hereinafter with reference to the drawings. In some drawings, illustration of part of members is omitted to clarify the illustration.

First Embodiment

[Configuration]

A first embodiment will be explained hereinafter with reference to FIG. 1A and FIG. 1B.

[Configuration 1 of Endoscopic System 5]

Figure 1A:
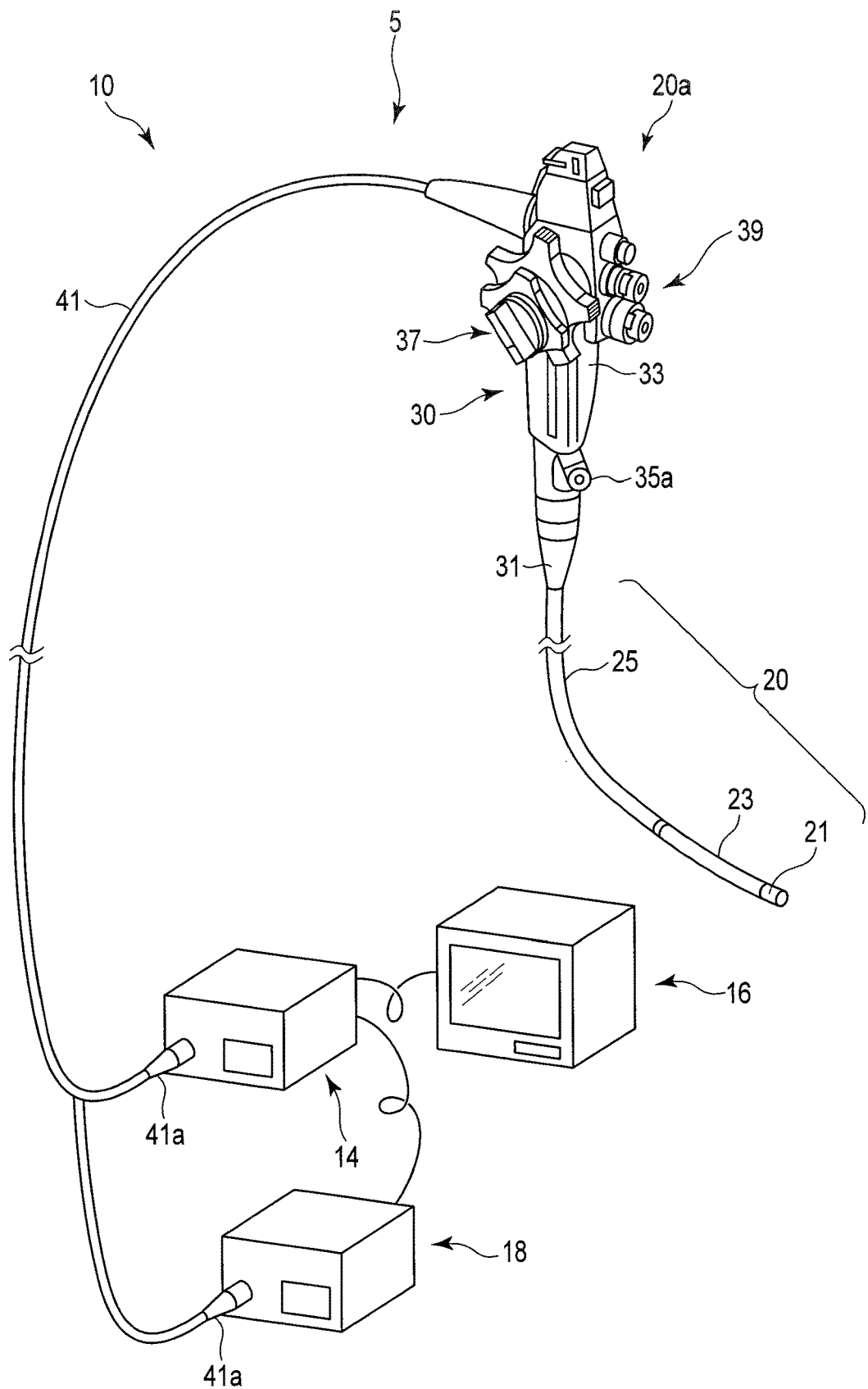
FIG. 1A is a perspective view of an endoscopic system according to a first embodiment of the present invention.

As illustrated in FIG. 1A, the endoscopic system 5 includes an endoscope 10 that irradiates an observed portion with illumination light, for example, to image the observed portion, and a controller 14 that is detachably connected to the endoscope 10. The observed portion is, for example, a diseased portion or a lesion portion in the body cavity.

The endoscopic system 5 further includes an image display 16 that is, for example, a monitor that is connected with the controller 14 and displays the observed portion imaged by the endoscope 10, and a light source device 18 that is detachably connected to the endoscope 10, also detachably connected to the controller 14, and emits light.

[Endoscope 10]

As illustrated in FIG. 1A, the endoscope 10 includes a hollow and elongated insertion unit 20 that is inserted into the body cavity or the like, and an operating unit 30 that is coupled with a proximal end portion of the insertion unit 20 and operates the endoscope 10.

[Insertion Unit 20]

As illustrated in FIG. 1A, the insertion unit 20 includes a distal end hard portion 21, a bending portion 23, and a flexible tube portion 25, from a distal end portion side of the insertion unit 20 to the proximal end portion side of the insertion unit 20. A proximal end portion of the distal end hard portion 21 is coupled with a distal end portion of the bending portion 23, and a proximal end portion of the bending portion 23 is coupled with a distal end portion of the flexible tube portion 25.

[Operating Unit 30]

As illustrated in FIG. 1A, the operating unit 30 includes a main body portion 31 from which the flexible tube portion 25 extends, a grasping portion 33 coupled with a proximal end portion of the main body portion 31 and grasped by the operator who operates the endoscope 10, and a universal cord 41 connected with the grasping portion 31.

[Main Body Portion 31]

As illustrated in FIG. 1A, the main body portion 31 includes a treatment instrument insertion port 35a. The treatment instrument insertion port 35a is coupled with a proximal end portion of a treatment instrument insertion channel (not illustrated). The treatment instrument insertion channel is disposed inside the insertion unit 20, and disposed to extend from the main body portion 31 to the distal end hard portion 21. A distal end portion of the treatment instrument insertion channel communicates with a distal end opening portion (not illustrated) disposed in the distal end hard portion 21. The treatment instrument insertion port 35a serves as an insertion port to insert an endoscope treatment instrument (not illustrated) into the treatment instrument insertion channel. The endoscope treatment instrument is inserted from the treatment instrument insertion port 35a into the treatment instrument insertion channel, and pushed into the distal end hard portion 21 side. The endoscope treatment instrument projects from the distal end opening portion.

[Grasping Portion 33]

As illustrated in FIG. 1A, the grasping portion 33 includes a bending operation portion 37 that operates and bends the bending portion 23, and a switch 39 for air feed, water feed, and endoscopic imaging.

[Universal Cord 41]

As illustrated in FIG. 1A, the universal cord 41 extends from a side surface of the grasping portion 33. The universal cord 41 has branched end portions, and each of the end portions is provided with a connection connector 41a. One of the connection connectors 41a is attachable to and detachable from the controller 14, and the other of the connection connectors 41a is attachable to and detachable from the light source device 18.

[Controller 14, Image Display 16, and Light Source Device 18]

The controller 14 controls the endoscope 10, the image display 16, and the light source device 18, and details of the control will be described later. The image display 16 and the light source device 18 will be described later.

[Insertion Unit 20 and Non-Insertion Unit 20a]

Figure 1B:
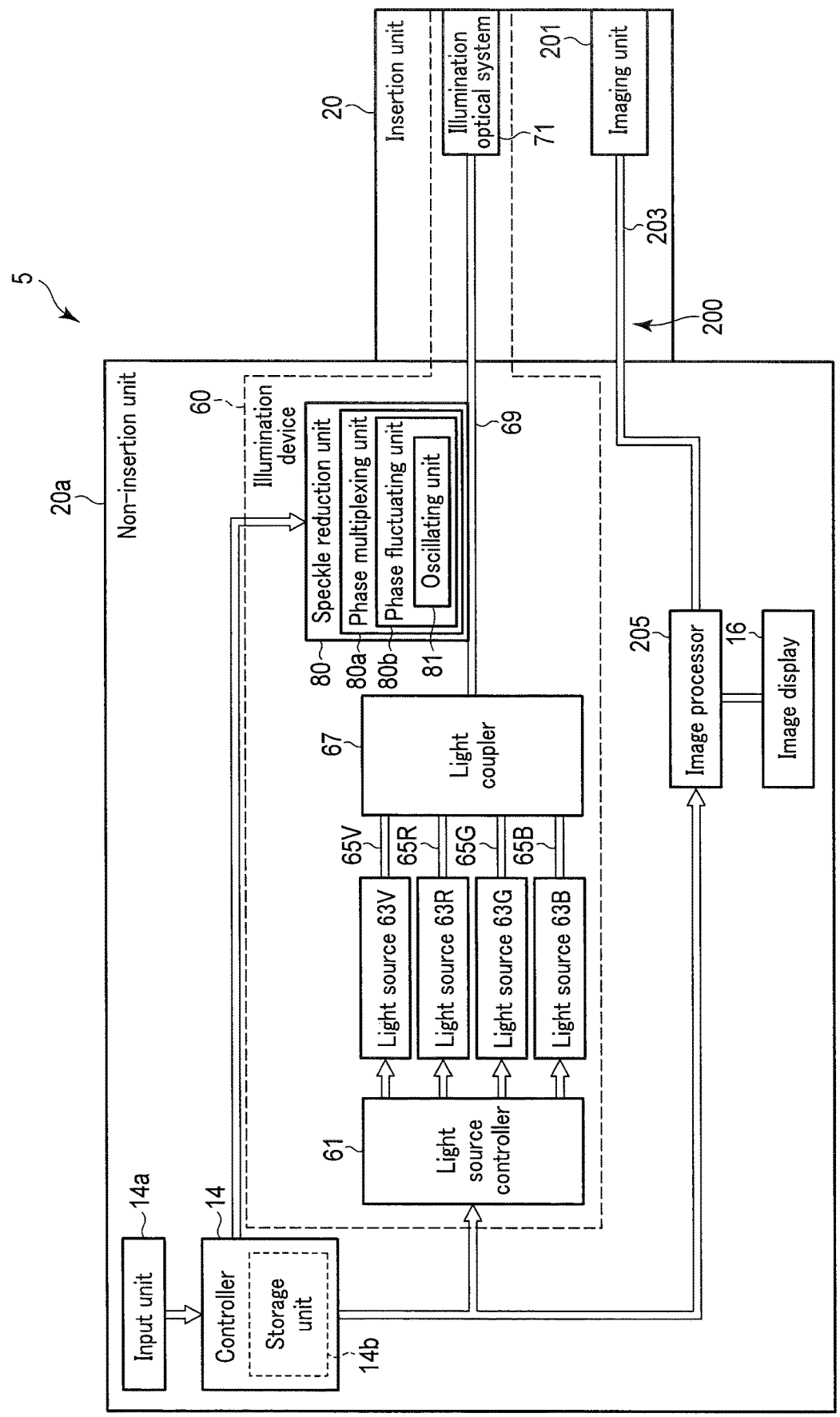
FIG. 1B is a schematic diagram of the endoscopic system according to the first embodiment.

As illustrated in FIG. 1A and FIG. 1B, the endoscopic system 5 includes the insertion unit 20 that is inserted into a desired region such as the body cavity, and a non-insertion unit 20a that is not inserted into the body cavity and is disposed in an outside the desired region. The non-insertion unit 20a includes the operating unit 30 serving as part of the endoscope 10, the controller 14, the image display 16, and the light source device 18.

[Configuration 2 of Endoscopic System 5]

The endoscopic system 5 of the present embodiment uses one of a plurality of observation modes including a speckle observation mode for observing the observed portion based on a speckle generated on the observed portion by light, when the observed portion is observed by the endoscopic system 5 using the light which has coherence. The observation mode includes, for example, a white-light observation mode which observes the observed portion using white light, the speckle observation mode which observes the observed portion based on the speckle and a special-light observation mode which observes the observed portion using special light.

For this reason, as illustrated in FIG. 1B, the endoscopic system 5 further includes an input unit 14a to which the operator inputs the observation mode, the controller 14 described above that performs control in accordance with the observation mode input by the input unit 14a, and an illumination device 60 that emits illumination light in accordance with the control of the controller 14.

As illustrated in FIG. 1B, the endoscopic system 5 further includes a speckle reduction unit 80, and an image acquisition unit 200 that acquires an image of the observed portion or the like in accordance with the observation mode, the speckle reduction unit 80 is disposed in the non-insertion unit 20a, and is stopped or driven in accordance with the observation mode, such that the speckle reduction unit does not reduce the speckle in the speckle observation mode, and reduces the speckle in observation modes other than the speckle observation mode, such as the white-light observation mode and the special-light observation mode.

As illustrated in FIG. 1B, the endoscopic system 5 further includes the image display 16 described above that displays an image acquired by the image acquisition unit 200.

[Input Unit 14a]

When the operator makes an input to the input unit 14a to designate an observation mode among the observation modes to perform observation, the input unit 14a inputs an instruction to perform observation with the observation mode input by the operator to the controller 14. The input unit 14a is disposed in the non-insertion unit 20a, for example, in the controller 14. The input unit 14a includes, for example, a switch unit to select the observation mode in a switchable manner.

[Controller 14]

As illustrated in FIG. 1B, the controller 14 includes a storage unit 14b that stores a control table in advance. The control table stores, for example, operations of the illumination device 60, operations of the speckle reduction unit 80, and operations of the image acquisition unit 200 in the respective observation modes.

When the controller 14 receives the observation mode input from the input unit 14a, the controller 14 controls the operation of the illumination device 60, the operation of the speckle reduction unit 80, and the operation of the image acquisition unit 200 in conjunction in accordance with the observation mode input from the input unit 14a to the controller 14, based on the control table. The controller 14 has, for example, a hardware circuitry including ASCI.

The following are operations of the illumination device 60, operations of the speckle reduction unit 80, and operations of the image acquisition unit 200 for the respective observation modes stored in the control table.

[White-Light Observation Mode]

Operation of the illumination device 60: only a light source 63R, a light source 63G, and a light source 63B of the illumination device 60 described later are driven to be turned on.

Operation of the speckle reduction unit 80: the speckle reduction unit 80 is driven. More specifically, an oscillating unit 81 of the speckle reduction unit 80 described later oscillates a light guide member 69 of the illumination device 60 described later.

Operation of the image acquisition unit 200: the image acquisition unit 200 performs image processing suitable for white light.

[Speckle Observation Mode]

Operation of the illumination device 60: only a light source 63V of the illumination device 60 described later is driven to be turned on.

Operation of the speckle reduction unit 80: the speckle reduction unit 80 is stopped.

Operation of the image acquisition unit 200: the image acquisition unit 200 performs image processing suitable for the speckle.

[Special-Light Observation Mode]

Operation of the illumination device 60: only the light source 63V and the light source 63G of the illumination device 60 are driven to be turned on.

Operation of the speckle reduction unit 80: the speckle reduction unit 80 is driven. More specifically, the oscillating unit 81 of the speckle reduction unit 80 oscillates the light guide member 69 of the illumination device 60.

Operation of the image acquisition unit 200: the image acquisition unit 200 performs image processing suitable for special light.

[Illumination Device 60]

As illustrated in FIG. 1B, the illumination device 60 includes a light source controller 61, the light source 63V, the light source 63R, the light source 63G, the light source 63B, a light guide member 65V, a light guide member 65R, a light guide member 65G, a light guide member 65B, a light coupler 67, the light guide member 69, and an illumination optical system 71.

The light source controller 61, the light source 63V, the light source 63R, the light source 63G, the light source 63B, the light guide member 65V, the light guide member 65R, the light guide member 65G, the light guide member 65B, and the light coupler 67 are incorporated in the light source device 18 included in the non-insertion unit 20a, for example.

The light guide member 69 is incorporated in, for example, the universal cord 41, the operating unit 30, the grasping portion 33, and the main body portion 31 that are included in the non-insertion unit 20a, and the insertion unit 20.

The illumination optical system 71 is incorporated in the distal end portion of the insertion unit 20.

[Light Source Controller 61]

The light source controller 61 controls the light source 63V, the light source 63R, the light source 63G, and the light source 63B so that each of the light source 63V, the light source 63R, the light source 63G, and the light source 63B drives or stops in accordance with the control of the controller 14, in other words, in accordance with the input observation mode. The light source controller 61 controls the driving current and the driving method for the light source 63V, the light source 63R, the light source 63G, and the light source 63B. The driving method controls continuous driving, pulse driving, and high-frequency superimposing. The light source controller 61 has, for example, a hardware circuitry including ASCI.

[Light Sources 63V, 63R, 63G, and 63B]

Each of the light sources 63V, 63R, 63G, and 63B emits light in accordance with the observation mode, as described above. Each of the light sources 63V, 63R, 63G, and 63B emits light having high coherence, such as laser light.

The light source 63V includes, for example, a laser diode that emits violet laser light. The wavelength of the laser light is, for example, 405 nm.

The light source 63B includes, for example, a laser diode that emits blue laser light. The wavelength of the laser light is, for example, 445 nm.

The light source 63G includes, for example, a laser diode that emits green laser light. The wavelength of the laser light is, for example, 515 nm.

The light source 63R includes, for example, a laser diode that emits red laser light. The wavelength of the laser light is, for example, 635 nm.

The light sources 63V, 63R, 63G, and 63B as described above emit lights that are optically different in accordance with the observation mode, as described above. For example, the light source 63V is shared between the respective observation modes, such that the violet laser light used for the speckle observation mode as described above is used for the special-light observation mode serving as at least one observation mode other than the speckle observation mode.

[Light Guide Members 65V, 65B, 65G, and 65R]

The light guide member 65V is optically connected with the light source 63V and the light coupler 67, and guides the laser light emitted from the light source 63V to the light coupler 67.

The light guide member 65B is optically connected with the light source 63B and the light coupler 67, and guides the laser light emitted from the light source 63B to the light coupler 67.

The light guide member 65G is optically connected with the light source 63G and the light coupler 67, and guides the laser light emitted from the light source 63G to the light coupler 67.

The light guide member 65R is optically connected with the light source 63R and the light coupler 67, and guides the laser light emitted from the light source 63R to the light coupler 67.

The light guide member 65V includes, for example, a single-wire optical fiber of a multi-mode fiber. The same is applicable to the light guide member 65R, the light guide member 65G, and the light guide member 65B.

A condensing lens (not illustrated) is disposed between the light source 63V and the light guide member 65V. The light emitted from the light source 63V is condensed to the light guide member 65V with the condensing lens. The same is also applicable to the light source 63R and the light guide member 65R, the light source 63G and the light guide member 65G, and the light source 63B and the light guide member 65B.

[Light Coupler 67]

The light coupler 67 couples the laser lights guided by the light guide member 65V, the light guide member 65R, the light guide member 65G, and the light guide member 65B.

For example, because the light sources 63R, 63G, and 63B are driven in the white-light observation mode, the light coupler 67 couples the blue laser light, the green laser light, and the red laser light in the white-light observation mode, to generate white light.

In addition, for example, because the light sources 63V and 63G are driven in the special-light observation mode, the light coupler 67 couples the violet laser light and the green laser light in the special-light observation mode, to generate special light.

For example, because only the light source 63V is driven in the speckle observation mode, the light coupler 67 lets the violet laser light pass therethrough in the speckle observation mode.

In the above operations, the light coupler 67 couples the laser lights into single illumination light, such that the respective laser lights are emitted as a single light from the illumination optical system. The light coupler 67 includes, for example, an optical fiber combiner.

[Light Guide Member 69]

The light guide member 69 optically connects the light coupler 67 with the illumination optical system 71, to guide the laser light coupled by the light coupler 67 to the illumination optical system 71. The light guide member 69 includes, for example, a single-wire optical fiber of a multi-mode.

[Illumination Optical System 71]

The illumination optical system 71 emits the laser light guided by the light guide member 69 to the observed portion with a desired light distribution. The illumination optical system 71 is the same for the respective observation modes, and shared between the respective observation modes. The illumination optical system 71 includes a plurality of lenses.

[Speckle Reduction unit 80]

Generally, when light having high coherence such as laser light is applied to the observed portion, the light is reflected and scattered in the vicinity of the surface of the observed portion. This causes overlapping of phases of the light, and causes an interference pattern reflecting the state in the vicinity of the surface. The interference pattern is referred to as speckle.

The speckle reduction unit 80 of the present embodiment reduces the speckle from the observed portion image displayed on the image display 16, in accordance with the observation mode; more specifically, in the observation modes other than the speckle observation mode, such as the white-light observation mode and the special-light observation mode.

For this reason, the speckle reduction unit 80 includes a phase multiplexing unit 80a that couples the phase by converting part of the laser light and generating laser light having a phase that is different from the original phase. The phase multiplexing unit 80a couples the phase to average the speckle in the observed portion image, and consequently reduce the speckle.

The phase multiplexing unit 80a includes a phase fluctuating unit 80b that temporally fluctuates the phase of the laser light such that a plurality of laser lights having mutually different phases are generated in phases that are temporally different. Specifically, the phase fluctuating unit 80b generates speckles that are temporally different in the vicinity of the surface of the observed portion. Temporally fluctuating the phase of the laser light is referred to as phase fluctuation. The speed of a period with which the phase fluctuating unit 80b temporally fluctuates the phase of light is faster than the frame rate (for example, 30 fps) of the image acquisition unit 200.

For this reason, the phase fluctuating unit 80b includes the oscillating unit 81 that oscillates the light guide member 69 that guides the laser light, for example, such that the phase of the laser light temporally fluctuates. The temporal fluctuation in the phase of the laser light indicates a speed of a period with which the phase of the laser light is temporally fluctuated, and serves as a time interval corresponding to a fluctuation frequency at which the oscillating unit 81 oscillates the light guide member 69. The fluctuation frequency is suitably faster than the frame rate (for example, 30 fps) of the image acquisition unit 200, and several times as fast as the frame rate. The oscillating unit 81 includes an actuator such as an electric motor and a piezoelectric substance. The oscillating unit 81 is controlled to be driven and stopped in accordance with the observation mode, more specifically, the oscillating unit 81 is controlled by the controller 14.

The speckle reduction unit 80 having the above configuration is disposed in the non-insertion unit 20a, for example, such that the oscillating unit 81 abuts against the light guide member 69.

[Image Acquisition Unit 200]

As illustrated in FIG. 1B, the image acquisition unit 200 includes an imaging unit 201 that images light that is emitted from the illumination optical system 71 and then reflected from the observed portion as an image, an imaging cable 203 that transmits the image imaged by the imaging unit 201, and an image processor 205 that processes the image transmitted by the imaging cable 203.

The imaging unit 201 is incorporated in the distal end portion of the insertion unit 20. The imaging unit 201 includes, for example, a CCD, and/or a CMOS.

The imaging cable 203 is incorporated in, for example, the universal cord 41, the operating unit 30, the grasping portion 33, and the main body portion 31 included in the non-insertion unit 20a, and the insertion unit 20.

The image processor 205 is disposed in the non-insertion unit 20a. The image processor 205 processes the image in accordance with the control of the controller 14, in other words, in accordance with the input observation mode. The image processor 205 has, for example, a hardware circuitry including ASCI.

The image acquired by the image processor 205 is also referred to as a frame, and the image processor 205 makes visualization by repeatedly acquiring frames. The speed at which frames are acquired is referred to as the frame rate, and the frame rate is, for example, 30 fps.

[Function]

The following is an explanation of functions in the white-light observation mode, the speckle observation mode, and the special-light observation mode.

[White-Light Observation Mode]

The input unit 14a is operated by the operator, and the white-light observation mode is input to the input unit 14a. The input unit 14a inputs an instruction that the observation mode is the white-light observation mode to the controller 14.

Based on the instruction, the controller 14 refers to the control table stored in the storage unit 14b, and controls the operation of the illumination device 60, the operation of the speckle reduction unit 80, and the operation of the image acquisition unit 200 in conjunction with each other.

In the white-light observation mode, the controller 14 controls the light source controller 61, such that the light source 63R, the light source 63G, and the light source 63B are driven to be turned on and the light source 63V is stopped. Based on the control of the controller 14, the light source controller 61 controls the light sources 63R, 63G, 63B, and 63V, such that the light source 63R, the light source 63G, and the light source 63B are driven to be turned on and the light source 63V is stopped. Thereby, the light source 63R emits red laser light, the light source 63G emits green laser light, and the light source 63B emits blue laser light. The red laser light is guided to the light coupler 67 by the light guide member 65R, the green laser light is guided to the light coupler 67 by the light guide member 65G, and the blue laser light is guided to the light coupler 67 by the light guide member 65B. The light coupler 67 couples these laser lights to generate white light. The white light is guided to the illumination optical system 71 by the light guide member 69.

In the white-light observation mode, the controller 14 controls the speckle reduction unit 80 such that the speckle reduction unit 80 is driven.

Accordingly, when the white light is guided to the illumination optical system 71 by the light guide member 69, the oscillating unit 81 of the speckle reduction unit 80 oscillates the light guide member 69. For this reason, the phase of the white light temporally fluctuates. Specifically, in the white light, a plurality of laser lights having phases different from each other are guided in a temporally different state.

The phase-fluctuated white light is converted into a desired light distribution by the illumination optical system 71. Thereafter, the white light is emitted from the illumination optical system 71, to be applied to the observed portion. In this state, in the white light, a plurality of laser lights having phases different from each other are applied in a temporally different state to the observed portion. For this reason, the speckle generated in the observed portion is temporally different. The temporal difference means that the speckle is different at time intervals corresponding to the fluctuation frequency at which the oscillating unit 81 oscillates the light guide member 69. This averages the speckle, and consequently reduces the speckle.

The imaging unit 201 images the light reflected from the observed portion as an image. The image is transmitted to the image processor 205 through the imaging cable 203. The image processor 205 performs image processing, such that an image obtained with white light generated only with three colors of RGB has a natural shade, to generate the observed portion image. The image display 16 displays the image.

The frame rate serving as an interval at which the image processor 205 acquires an image is several fractions or more slower than the fluctuation frequency at which the oscillating unit 81 oscillates the light guide member 69. Accordingly, in the generated observed portion image, the different speckles generated in the frame rate are averaged, and the speckle is reduced.

[Speckle Observation Mode]

The input unit 14*a* is operated by the operator, and the speckle observation mode is input to the input unit 14*a*. The input unit 14*a* inputs an instruction that the observation mode is the speckle observation mode to the controller 14.

Based on the instruction, the controller 14 refers to the control table stored in the storage unit 14*b*, and controls the operation of the illumination device 60, the operation of the speckle reduction unit 80, and the operation of the image acquisition unit 200 in conjunction.

In the speckle observation mode, the controller 14 controls the light source controller 61, such that the light source 63V is driven to be turned on and the light source 63R, the light source 63G, and the light source 63B are stopped. Based on the control of the controller 14, the light source controller 61 controls the light sources 63R, 63G, 63B, and 63V, such that the light source 63V is driven to be turned on and the light source 63R, the light source 63G, and the light source 63B are stopped. Thereby, the light source 63V emits violet laser light. The violet laser light is guided to the light coupler 67 by the light guide member 65V, passes through the light coupler 67, and is guided to the illumination optical system 71 by the light guide member 69.

In the speckle observation mode, the controller 14 controls the speckle reduction unit 80 such that the speckle reduction unit 80 is stopped.

Accordingly, the violet laser light is converted into a desired light distribution by the illumination optical system 71. Thereafter, the violet laser light is emitted from the illumination optical system 71, to be applied to the observed portion. Because the oscillating unit 81 of the speckle reduction unit 80 does not act on the violet laser light, speckle is generated in the observed portion irradiated with the violet laser light.

The imaging unit 201 images the light reflected from the observed portion as an image. The image is transmitted to the image processor 205 through the imaging cable 203. The image processor 205 performs image processing, such that the state of the observed portion is analyzed with the speckle, to generate the observed portion image. The image display 16 displays the image.

[Special-Light Observation Mode]

The input unit 14*a* is operated by the operator, and the special-light observation mode is input to the input unit 14*a*. The input unit 14*a* inputs an instruction that the observation mode is the special-light observation mode to the controller 14.

Based on the instruction, the controller 14 refers to the control table stored in the storage unit 14*b*, and controls the operation of the illumination device 60, the operation of the speckle reduction unit 80, and the operation of the image acquisition unit 200 in conjunction.

In the special-light observation mode, the controller 14 controls the light source controller 61, such that the light source 63V and the light source 63G are driven to be turned on and the light source 63R and the light source 63B are stopped. Based on the control of the controller 14, the light source controller 61 controls the light sources 63R, 63G, 63B, and 63V, such that the light source 63V and the light source 63G are driven to be turned on and the light source 63R and the light source 63B are stopped. Thereby, the light source 63V emits violet laser light, and the light source 63G emits green laser light. The violet laser light is guided to the light coupler 67 by the light guide member 65V, and the green laser light is guided to the light coupler 67 by the light guide member 65G. The light coupler 67 couples these laser lights to generate special light. The special light is guided to the illumination optical system 71 by the light guide member 69.

In the special-light observation mode, the controller 14 controls the speckle reduction unit 80 such that the speckle reduction unit 80 is driven.

Accordingly, when the special light is guided to the illumination optical system 71 by the light guide member 69, the oscillating unit 81 of the speckle reduction unit 80 oscillates the light guide member 69. For this reason, the phase of the special light temporally fluctuates. Specifically, in the special light, a plurality of laser lights having phases different from each other are guided in a temporally different state.

The phase-fluctuated special light is converted into a desired light distribution by the illumination optical system 71. Thereafter, the special light is emitted from the illumination optical system 71, to be applied to the observed portion. In this state, in the special light, a plurality of laser lights having phases different from each other are applied in a temporally different state to the observed portion. For this reason, the speckle generated in the observed portion is temporally different. The temporal difference means that the speckle is different at time intervals corresponding to the fluctuation frequency at which the oscillating unit 81 oscillates the light guide member 69. This averages the speckle, and consequently reduces the speckle.

The imaging unit 201 images the light reflected from the observed portion as an image. The image is transmitted to the image processor 205 through the imaging cable 203. Generally, violet laser light has a property of being strongly absorbed by hemoglobin in capillaries in the vicinity of the living tissue, and green laser light has a property of being strongly absorbed by hemoglobin in thick blood vessels in a deep portion of the living tissue. Based on these properties, the image processor 205 performs image processing, such that a contrast between the capillaries and the thick blood vessels is emphasized, to generate the observed portion image. The image display 16 displays the image.

The frame rate serving as an interval at which the image processor 205 acquires an image is several fractions or more slower than the fluctuation frequency at which the oscillating unit 81 oscillates the light guide member 69. Accordingly, in the generated observed portion image, the different speckles generated in the frame rate are averaged, and consequently the speckle is reduced.

[Effects]

In the present embodiment, the speckle reduction unit 80 is stopped or driven according to the observation mode, such that the speckle reduction unit 80 in the speckle observation mode does not reduce the speckle and the speckle reduction unit 80 reduces the speckle in the observation modes other than the speckle observation mode, such as the white-light observation mode and the special-light observation mode.

In the present embodiment, in each of the observation modes, the illumination light is emitted from the same illumination optical system 71.

In the present embodiment, no optical probe is used, and neither treatment instrument insertion port 35a nor treatment instrument insertion channel is used, but the treatment instrument can be used.

In the present embodiment, because it is unnecessary to incorporate an optical probe in the insertion unit 20, the diameter of the insertion unit 20 is not increased, and no strain is put on the patient.

Accordingly, the present embodiment enables execution of speckle observation and ordinary observation including white-light observation and special-light observation in a switchable manner, without using the treatment instrument insertion port 35a or the treatment instrument insertion channel, and without an increase in the diameter of the insertion unit 20.

In the present embodiment, because the speckle reduction unit 80 is stopped in the speckle observation mode, speckle is surely generated in the observed portion, and speckle can be sufficiently observed in the observed portion.

In the present embodiment, because the speckle reduction unit 80 is driven in the observation modes other than the speckle observation mode, such as the white-light observation mode and the special-light observation mode, the speckle can be surely reduced. Accordingly, the present embodiment can present deterioration of the observed portion image by speckle in the observation modes other than the speckle observation mode, such as the white-light observation mode and the special-light observation mode.

In the present embodiment, illumination light can be emitted to an outside from the same illumination optical system 71 by virtue of the light coupler 67, even when laser lights to be used are different between the observation modes in the speckle observation mode, the white-light observation mode and the special-light observation mode. The above feature simplifies the configuration in the present embodiment.

In the present embodiment, the light sources 63V, 63R, 63G, and 63B emit light having high coherence. With this configuration, the present embodiment enables the light to be efficiently made incident in the light guide members 65V, 65R, 65G, and 65B, and efficiently and optically couples the light sources 63V, 63R, 63G, and 63B with the light guide members 65V, 65R, 65G, and 65B. The present embodiment can reduce the diameter of the insertion unit 20, and brighten the illumination light. In addition, the present embodiment enables execution of the speckle observation mode and the observation modes other than the speckle observation mode, such as the white-light observation mode and the special-light observation mode as described above, and provides the endoscope 10 with high illumination performance for a plurality of observation modes.

The present embodiment also enables execution of white-light observation having the above laser-light effects, by using white light generated by laser light of three colors of R, G, and B, in the white-light observation mode.

In the present embodiment, when the controller 14 receives an input of the observation mode from the input unit 14a, the controller 14 controls the operation of the illumination device 60, the operation of the speckle reduction unit 80, and the operation of the image acquisition unit 200 in conjunction in accordance with the observation mode input to the controller 14, based on the control table. Accordingly, the present embodiment enables control of the operation of the illumination device 60, the operation of the speckle reduction unit 80, and the operation of the image acquisition unit 200 in conjunction with each other, and efficient switching of the observation modes.

In the present embodiment, the phase is multiplexed by the phase multiplexing unit 80a. In this manner, the present embodiment can average the speckle, reduces the speckle in the observed portion image, and prevent the deterioration of the observed portion image by speckle.

In the present embodiment, the fluctuation frequency at which the oscillation unit 81 oscillates the light guide member 69 is faster than the frame rate of the image acquisition unit 200. Accordingly, the present embodiment can temporally average the speckle in the observed portion image, consequently reduce the speckle, and prevent deterioration of the observed portion image by speckle.

In the present embodiment, the oscillating unit 81 oscillates the light guide member 69. In this manner, the present embodiment enables phase multiplexing and phase fluctuation. In the present embodiment, providing only the oscillating unit 81 can prevent a large decrease in light transmittance in the light guide member 69, suppress addition of members to the minimum, and prevent an increase in size of the endoscope 10 itself.

In the present embodiment, the oscillating unit 81 oscillates the light guide member 69 disposed at more distal end to the light coupler 67. In this manner, the present embodiment enables oscillation of a plurality of types of laser lights together with one oscillating unit 81, saves space, and reduces cost.

Generally, the diameter of a core of the light guide member 69 is larger than the diameter of cores of the light guide members 65V, 65R, 65G, and 65B. In addition, generally, the number of phases for which light can be guided increases as the diameter of the core increases. Accordingly, providing the oscillating unit 81 in the light guide member 69 rather than the light guide members 65V, 65R, 65G, and 65B can increase the effect of phase multiplexing, effectively reduce the speckle, and prevent deterioration of the observed portion image by speckle.

In the present embodiment, the special-light observation mode enables observation with an emphasized contrast between capillaries on the surface of the living tissue and thick blood vessels in the deep part.

In the present embodiment, in the speckle observation mode and the observation modes other than the speckle observation mode, such as the white-light observation mode and the special-light observation mode, the laser light in the respective observation modes is emitted from the shared illumination optical system 71. With this configuration, the present embodiment enables use of the same optical source, saves space, and reduces cost, in the case where the characteristic of the laser light used in speckle observation is the same as the characteristic of the laser light used in the observation modes other than the speckle observation mode, such as the white-light observation mode and the special-light observation mode.

[Others]

The light sources 63R, 63G, 63B, and 63V are not necessarily limited to emitting laser light. It suffices that the light sources 63R, 63G, 63B, and 63V emit light with coherence to generate speckle in the observed portion.

The light coupler 67 may include a spatial optical system that couples light.

The illumination optical system 71 may include a diffusion member that diffuses laser light to spread a light distribution.

The oscillating unit 81 may oscillate the optical member by providing the optical member including at least one of a lens, a diffusion plate, and a polarizing plate and disposed on the optical path of the laser light with movement such as vibrations and rotation in a desired direction.

The observation modes may include a mode of applying white light with a different hue, a mode of performing another publicly-known special-light observation to display the observed portion in an emphasized state, and a fluorescence observation mode for observing fluorescence generated when excitation light is applied to the observed portion or a medicine.

Second Embodiment

[Configuration]

Figure 2:
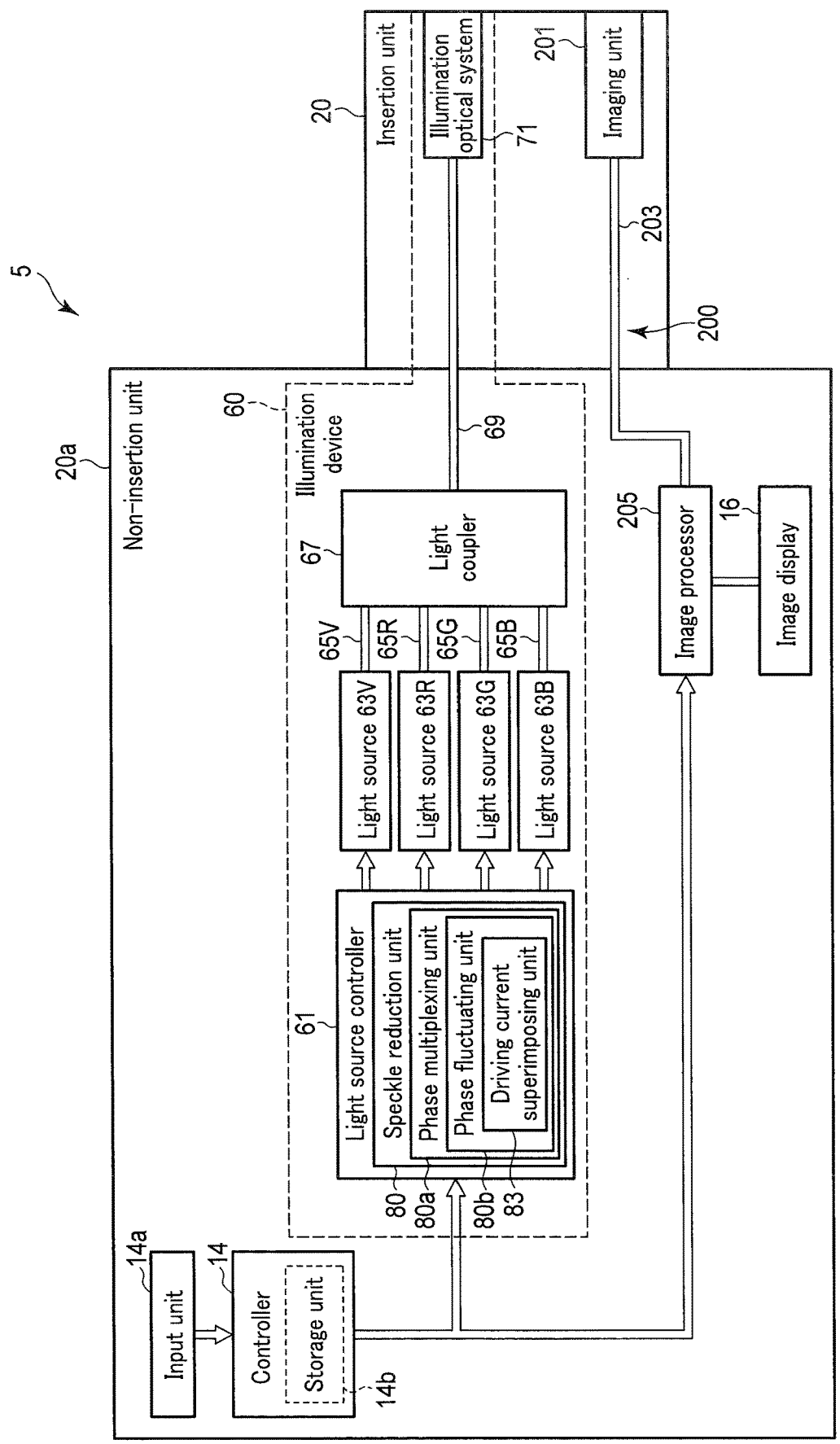
FIG. 2 is a schematic diagram of an endoscopic system according to a second embodiment.

The following is an explanation of only points that are different from the first embodiment, with reference to FIG. 2.

[Speckle Reduction Unit 80]

In the present embodiment, a phase fluctuating unit 80b of the speckle reduction unit 80 includes a driving current superimposing unit 83, instead of the oscillating unit 81, the driving current superimposing unit 83 is disposed in the light source controller 61, and periodically changes the driving current for the light sources 63V, 63R, 63G, and 63B in a range in which the phase of the laser light changes.

With periodical change of the driving current by the driving current superimposing unit 83, the output of the laser light periodically changes in the light sources 63V, 63R, 63G, and 63B. The phase of the laser light differs between the low-output side of the laser light and the high-output side of the laser light. In this manner, the phase of the laser light temporally fluctuates by periodical change of the driving current, thereby it causes temporally different speckle, averages the speckle, and consequently reduces the speckle.

A change of the driving current in a period, that is, the superimposing frequency of the driving current is faster than the frame rate (for example, 30 fps) of the image acquisition unit 200. In addition, the superimposing frequency of the driving current is fast enough to prevent visual recognition of light and shade caused by a periodical change in the driving current that is, by periodical change in output of the laser light, in the observed portion image. Superimposing a high frequency from several megahertz to several gigahertz is preferable because it spreads the spectrum of the laser light.

The driving current superimposing unit 83 is driven or stopped in accordance with the control of a controller 14, that is, the observation mode. The driving current superimposing unit 83 includes a circuit.

[Controller 14]

The following is an explanation of operations of an illumination device 60, operations of the speckle reduction unit 80, and operations of the image acquisition unit 200 for the respective observation modes stored in the control table.

[White-Light Observation Mode]

Operation of the illumination device 60: only the light source 63R, the light source 63G, and the light source 63B are driven to be turned on.

Operation of the speckle reduction unit 80: the speckle reduction unit 80 is driven. More specifically, the driving current superimposing unit 83 of the speckle reduction unit 80 superimposes the driving current only for the light sources 63R, 63G, and 63B.

Operation of the image acquisition unit 200: the image acquisition unit 200 performs image processing suitable for white light.

[Speckle Observation Mode]

Operation of the illumination device 60: only the light source 63V is driven to be turned on.

Operation of the speckle reduction unit 80: the speckle reduction unit 80 is stopped.

Operation of the image acquisition unit 200: the image acquisition unit 200 performs image processing suitable for the speckle.

[Special-Light Observation Mode]

Operation of the illumination device 60: only the light source 63V and the light source 63G are driven to be turned on.

Operation of the speckle reduction unit 80: the speckle reduction unit 80 is driven. More specifically, the driving current superimposing unit 83 of the speckle reduction unit 80 superimposes the driving current only for the light sources 63V and 63G.

Operation of the image acquisition unit 200: the image acquisition unit 200 performs image processing suitable for special light.

[Function]

The following is an explanation of functions in the white-light observation mode, the speckle observation mode, and the special-light observation mode. The following is an explanation of only points different from the first embodiment.

[White-Light Observation Mode]

In the white-light observation mode, the controller 14 controls the light source controller 61 such that the light source 63R, the light source 63G, and the light source 63B are driven to be turned on and the light source 63V is stopped. Based on the control of the controller 14, the light source controller 61 controls the light sources 63R, 63G, 63B, and 63V, such that the light source 63R, the light source 63G, and the light source 63B are driven to be turned on and the light source 63V is stopped. Thereby, the light source 63R emits red laser light, the light source 63G emits green laser light, and the light source 63B emits blue laser light. The red laser light is guided to the light coupler 67 by the light guide member 65R, the green laser light is guided to the light coupler 67 by the light guide member 65G, and the blue laser light is guided to the light coupler 67 by the light guide member 65B. The light coupler 67 couples these laser lights to generate white light. The white light is guided to the illumination optical system 71 by the light guide member 69.

In the white-light observation mode, the controller 14 controls the speckle reduction unit 80 such that the speckle reduction unit 80 is driven.

Accordingly, when the light source controller 61 controls the light sources 63R, 63G, and 63B, the driving current superimposing unit 83 of the speckle reduction unit 80 periodically changes the driving current for the light sources 63R, 63G, and 63B. For this reason, the phases of the respective laser lights emitted from the light sources 63R, 63G, and 63B temporally fluctuate. This configuration averages the speckle, and consequently reduces the speckle.

When a high frequency is superimposed, the spectrum of the laser light is spread, coherence of the laser light is reduced, and the speckle is further reduced.

The frame rate serving as an interval at which an image processor 205 acquires an image is several fractions or more slower than the superimposing frequency of the driving current. Accordingly, in the generated observed portion image, the different speckles generated in the frame rate are averaged, and the speckle is reduced. In addition, no light or shade caused by periodical change in the driving current is visually recognized in the observed portion image.

[Speckle Observation Mode]

This mode is substantially the same as that in the first embodiment.

[Special-Light Observation Mode]

In the special-light observation mode, the controller 14 controls the light source controller 61, such that the light source 63V and the light source 63G are driven to be turned on and the light source 63R and the light source 63B are stopped. Based on the control of the controller 14, the light source controller 61 controls the light sources 63R, 63G, 63B, and 63V, such that the light source 63V and the light source 63G are driven to be turned on and the light source 63R and the light source 63B are stopped. Thereby, the light source 63V emits violet laser light, and the light source 63G emits green laser light. The violet laser light is guided to the light coupler 67 by the light guide member 65V, and the green laser light is guided to the light coupler 67 by the light guide member 65G. The light coupler 67 couples these laser lights to generate special light. The special light is guided to the illumination optical system 71 by the light guide member 69.

In the special-light observation mode, the controller 14 controls the speckle reduction unit 80 such that the speckle reduction unit 80 is driven.

Accordingly, when light source controller 61 controls the light sources 63V and 63G, the driving current superimposing unit 83 of the speckle reduction unit 80 periodically changes the driving current for the light sources 63V and 63G. For this reason, the phases of the respective laser lights emitted from the light sources 63V and 63G temporally fluctuate. This configuration averages the speckle, and consequently reduces the speckle.

When a high frequency is superimposed, the spectrum of the laser light is spread, coherence of the laser light is reduced, and the speckle is further reduced.

The frame rate serving as an interval at which the image processor 205 acquires an image is several fractions or more slower than the superimposing frequency of the driving current. Accordingly, in the generated observed portion image, the different speckles generated in the frame rate are averaged, and the speckle is reduced. In addition, no light or shade caused by periodical change in the driving current is visually recognized in the observed portion image.

[Effects]

In the present embodiment, the speckle can be reduced in the same manner as the first embodiment, with the driving current superimposing unit 83. In the present embodiment, providing only the driving current superimposing unit 83 in the light source controller 61 can suppress addition of members to the minimum, and prevent an increase in size of the endoscope 10 itself.

In addition, in the present embodiment, the superimposing frequency of the driving current is faster than the frame rate of the image acquisition unit 200. This can prevent visual recognition of light and shade caused by driving current superimposing in the observed portion image.

In the present embodiment, superimposing a high frequency can spread the spectrum of the laser light, reduce coherence of the laser light, and further reduce the speckle. With this configuration, the present embodiment can prevent deterioration of the observed portion image by speckle.

Third Embodiment

[Configuration]

Figure 3B:
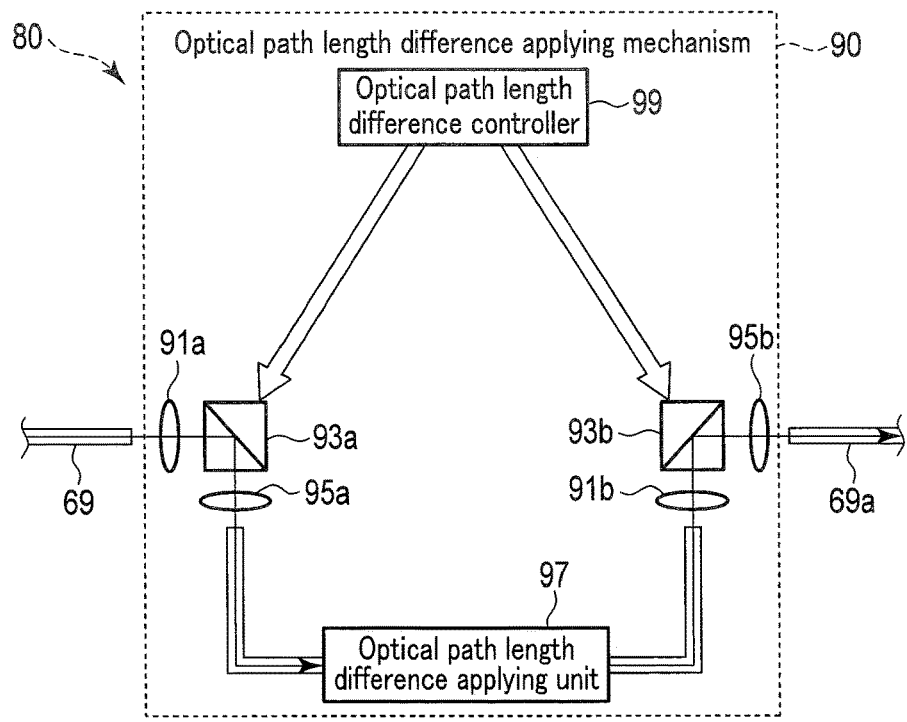
FIG. 3B is a diagram illustrating an arrangement position of an optical path length difference applying mechanism in a white-light observation mode and in a special-light observation mode.
Figure 3C:
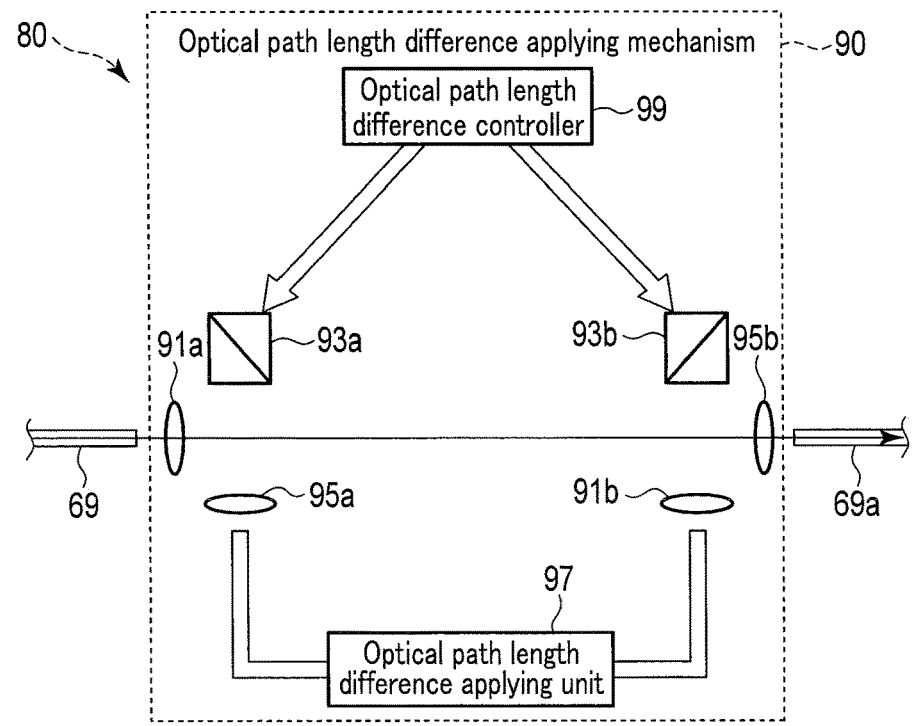
FIG. 3C is a diagram illustrating an arrangement position of the optical path length difference applying mechanism in a speckle observation mode.

The following is an explanation of only points different from the first embodiment, with reference to FIG. 3A, FIG. 3B, and FIG. 3C.

[Speckle Reduction Unit 80]

The speckle reduction unit 80 includes an optical path length difference applying mechanism 90 that applies an optical path length difference to the laser light, to reduce the speckle in observation modes other than the speckle observation mode, such as the white-light observation mode and the special-light observation mode. The optical path length difference applying mechanism 90 is disposed in the non-insertion unit 20a.

The optical path length difference applying mechanism 90 includes a parallel member 91a including, for example, a lens that converts laser light emitted from a light guide member 69 into parallel light, a reflecting member 93a that reflects the parallel light converted by the parallel member 91a, and a condensing member 95a including, for example, a lens that condenses the laser light reflected by the reflecting member 93a. The reflecting member 93a includes, for example, a movable mirror.

The optical path length difference applying mechanism 90 further includes an optical path length difference applying unit 97 on which the laser light condensed by the condensing member 95a is made incident, in the observation modes other than the speckle observation mode, such as the white-light observation mode and the special-light observation mode. The optical path length difference applying unit 97 divides the laser light into a plurality of luminous fluxes, and provides the luminous fluxes with respective optical path lengths different from each other. For this reason, the optical path length difference is generated between the luminous fluxes. The optical path length difference applying unit 97 also couples the luminous fluxes having different optical path lengths.

The optical path length difference applying unit 97 as described above includes, for example, a bundle fiber including a plurality of fibers having different lengths each other. In the bundle fiber, the number of the fibers is, for example, several hundred to several thousand. In the present embodiment, the difference in length between the fibers is longer than the coherence length of the laser lights used in the white-light observation mode and the special-light observation mode, to prevent mutual interference between white lights and occurrence of speckle due to interference in the observed portion, in the observation modes other than the speckle observation mode, such as the white-light observation mode and the special-light observation mode. For this reason, in the optical path length difference applying unit 97, the laser light made incident in the bundle fiber in the white-light observation mode and the special-light observation mode has an optical path length difference longer than the coherence length. In other words, in the white-light observation mode and the special-light observation mode, the laser light is provided with an optical path length difference longer than the coherence length by the optical path length difference applying unit 97.

The optical path length difference applying mechanism 90 further includes a parallel member 91b including a lens that converts laser light emitted from the optical path length difference applying unit 97 into parallel light, and a reflecting member 93b that reflects the parallel light converted by the parallel member 91b. The optical path length difference applying mechanism 90 further includes a condensing member 95b that condenses the laser light reflected by the reflecting member 93b to a light guide member 69a that guides the light to an illumination optical system 71. The parallel member 91b and the condensing member 95b include, for example, a mirror. The reflecting member 93b includes, for example, a movable mirror.

The optical path length difference applying mechanism 90 further includes an optical path length difference controller 99 that controls, for example, the reflecting members 93a and 93b of the optical path length difference applying mechanism 90, in accordance with the control of the controller 14, that is, the observation mode. The optical path length difference controller 99 moves the reflecting members 93a and 93b such that the reflecting members 93a and 93b are arranged on or an outside the optical path of the speckle reduction unit 80, in accordance with the observation mode.

As illustrated in FIG. 3A and FIG. 3B, when the reflecting members 93a and 93b are arranged on the optical path of the speckle reduction unit 80, the parallel light converted by the parallel member 91a is reflected by the reflecting member 93a toward the condensing member 95a. In addition, the parallel light converted by the parallel member 91b is reflected by the reflecting member 93b toward the condensing member 95b.

As illustrated in FIG. 3C, when the reflecting members 93a and 93b are arranged the outside the optical path of the speckle reduction unit 80, the parallel light converted by the parallel member 91a travels directly to condensing member 95b.

[Controller 14]

The following explains operations of an illumination device 60, operations of the speckle reduction unit 80, and operations of an image acquisition unit 200 stored in the control table.

[White-Light Observation Mode]

Operation of the illumination device 60: only a light source 63R, a light source 63G, and a light source 63B are driven to be turned on.

Operation of the speckle reduction unit 80: the speckle reduction unit 80 is driven. More specifically, as illustrated in FIG. 3A and FIG. 3B, the optical path length difference controller 99 of the speckle reduction unit 80 moves the reflecting members 93a and 93b onto the optical path of the speckle reduction unit 80.

Operation of the image acquisition unit 200: the image acquisition unit 200 performs image processing suitable for white light.

[Speckle Observation Mode]

Operation of the illumination device 60: only a light source 63V is driven to be turned on.

Operation of the speckle reduction unit 80: the speckle reduction unit 80 is driven. More specifically, as illustrated in FIG. 3C, the optical path length difference controller 99 of the speckle reduction unit 80 moves the reflecting members 93a and 93b to an outside of the optical path of the speckle reduction unit 80.

Operation of the image acquisition unit 200: the image acquisition unit 200 performs image processing suitable for the speckle.

[Special-Light Observation Mode]

Operation of the illumination device 60: only the light source 63V and the light source 63G are driven to be turned on.

Operation of the speckle reduction unit 80: the speckle reduction unit 80 is driven. More specifically, as illustrated in FIG. 3A and FIG. 3B, the optical path length difference controller 99 of the speckle reduction unit 80 moves the reflecting members 93a and 93b onto the optical path of the speckle reduction unit 80.

Operation of the image acquisition unit 200: the image acquisition unit 200 performs image processing suitable for special light.

[Function]

The following is an explanation of functions in the white-light observation mode, the speckle observation mode, and the special-light observation mode. The following is an explanation of only points different from the first embodiment.

[White-Light Observation Mode]

In the white-light observation mode, the controller 14 controls the speckle reduction unit 80 to drive the speckle reduction unit 80.

For this reason, as illustrated in FIG. 3A and FIG. 3B, the optical path length difference controller 99 of the speckle reduction unit 80 moves the reflecting members 93a and 93b onto the optical path of the speckle reduction unit 80.

In this manner, the white light emitted from the light guide member 69 is made incident in the optical path length difference applying unit 97 via the parallel member 91a, the reflecting member 93a, and the condensing member 95a. Thereafter, the white light is provided with an optical path length difference by the optical path length difference applying unit 97.

The white light provided with the optical path length difference travels to the illumination optical system 71 via the parallel member 91b, the reflecting member 93b, the condensing member 95b, and the light guide member 69a. The white light is converted into a desired light distribution by the illumination optical system 71. The white light is emitted from the illumination optical system 71, and applied to the observed portion.

The white light is provided with an optical path length difference longer than the coherence length by the optical path length difference applying unit 97. Accordingly, the white lights do not interfere with each other, and occurrence of speckle is prevented in the observed portion.

[Speckle Observation Mode]

In the white-light observation mode, the controller 14 controls the speckle reduction unit 80 to drive the speckle reduction unit 80.

For this reason, as illustrated in FIG. 3C, the optical path length difference controller 99 of the speckle reduction unit 80 moves the reflecting members 93a and 93b to the outside of the optical path of the speckle reduction unit 80.

In this manner, the violet laser light emitted from the light guide member 69 is made incident in the light guide member 69a via the parallel member 91a and the condensing member 95b. The violet laser light is not made incident in the optical path length difference applying unit 97.

The violet laser light is converted into a desired light distribution by the illumination optical system 71. The violet laser light is emitted from the illumination optical system 71, and applied to the observed portion. Because the violet laser light is not provided with any optical path length difference, speckle occurs in the observed portion.

[Special-Light Observation Mode]

In the special-light observation mode, the controller 14 controls the speckle reduction unit 80 to drive the speckle reduction unit 80.

For this reason, as illustrated in FIG. 3A and FIG. 3B, the optical path length difference controller 99 of the speckle reduction unit 80 moves the reflecting members 93a and 93b onto the optical path of the speckle reduction unit 80.

In this manner, the special light emitted from the light guide member 69 is made incident in the optical path length difference applying unit 97 via the parallel member 91a, the reflecting member 93a, and the condensing member 95a. Thereafter, the special light is provided with an optical path length difference by the optical path length difference applying unit 97.

The special light provided with the optical path length difference travels to the illumination optical system 71 via the parallel member 91b, the reflecting member 93b, the condensing member 95b, and the light guide member 69a. The special light is converted into a desired light distribution by the illumination optical system 71. The special light is emitted from the illumination optical system 71, and applied to the observed portion.

The special light is provided with an optical path length difference longer than the coherence length by the optical path length difference applying unit 97. Accordingly, the special lights do not interfere with each other, and occurrence of speckle is prevented in the observed portion.

[Effects]

In the present embodiment, the optical path length difference applying unit 97 can provides the laser light with an optical path length difference longer than the coherence length, in the observation modes other than the speckle observation mode, such as the white-light observation mode and the special-light observation mode. Accordingly, the present embodiment can prevent mutual interference between laser lights, and prevent generation of speckle, in the white-light observation mode and the special-light observation mode. With this configuration, the present embodiment can surely prevent deterioration of the observed portion image by speckle.

Figure 3D:
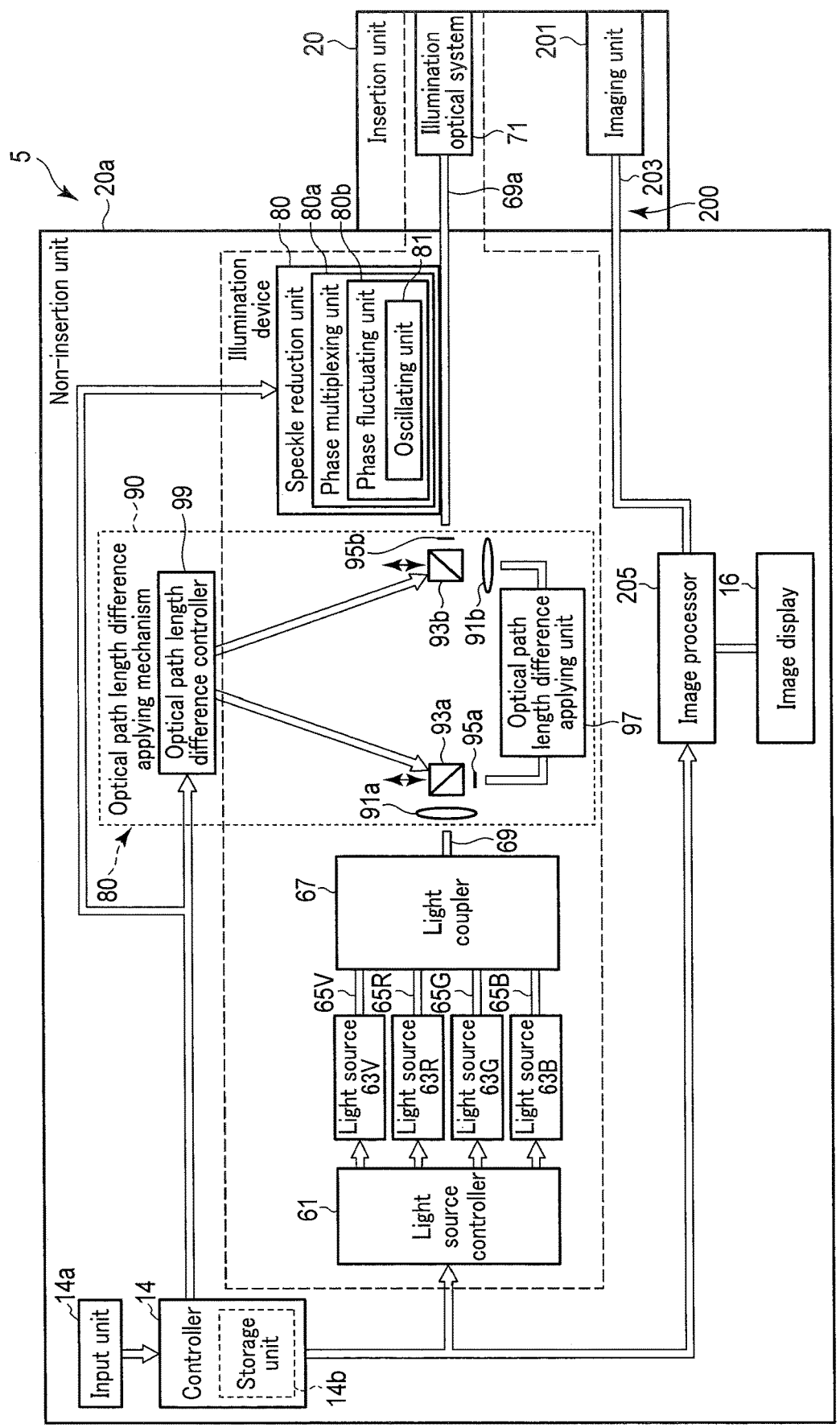
FIG. 3D is a schematic diagram of an endoscopic system according to a modification of the third embodiment.

As illustrated in FIG. 3D, the configuration of the present embodiment may be combined with the configuration of the first embodiment. Specifically, the speckle reduction unit 80 may include the oscillating unit 81 and the optical path length difference applying mechanism 90.

Figure 3E:
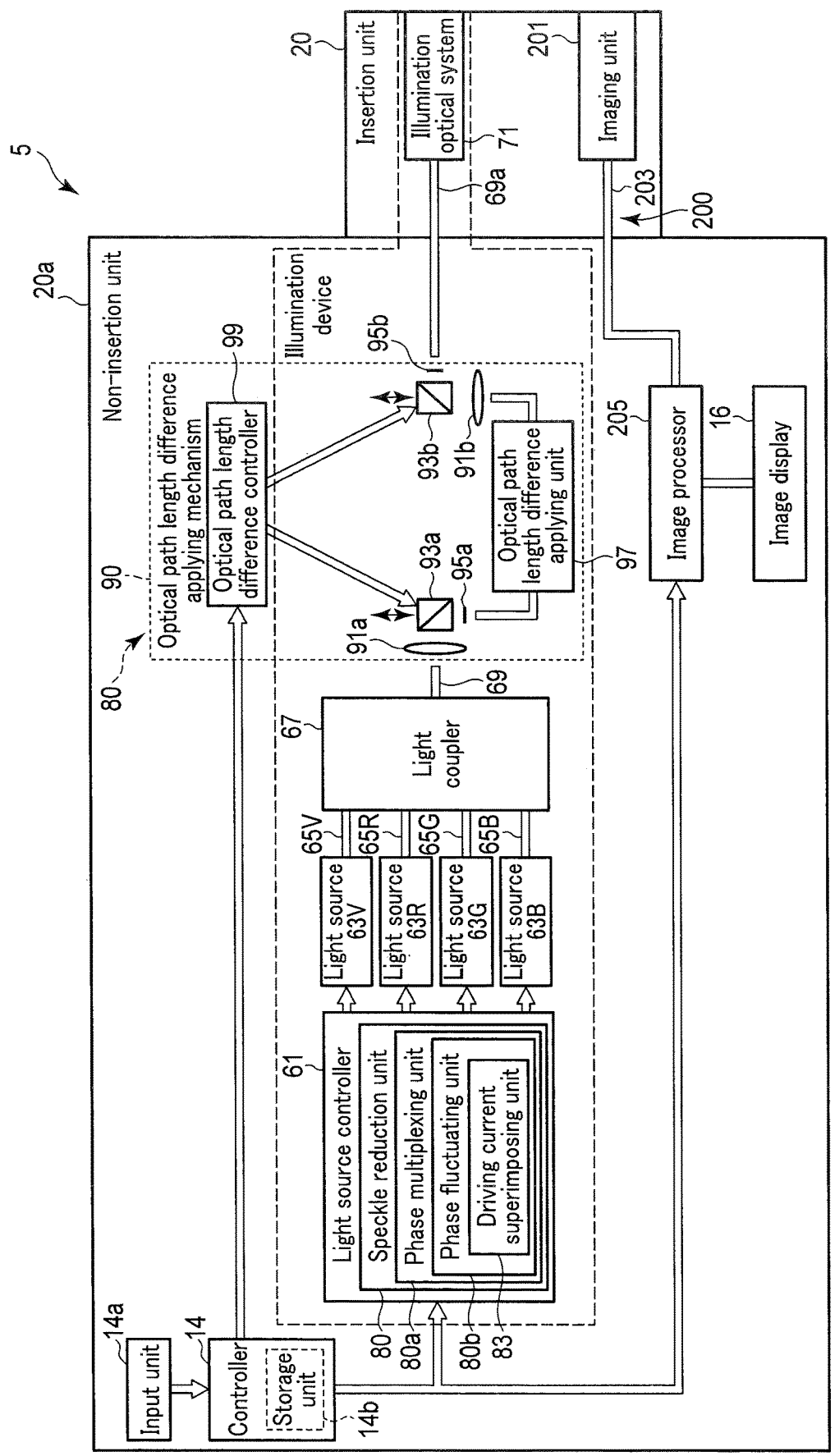
FIG. 3E is a schematic diagram of an endoscopic system according to a modification of the third embodiment.

As illustrated in FIG. 3E, the configuration of the present embodiment may be combined with the configuration of the second embodiment. Specifically, the speckle reduction unit 80 may include the driving current superimposing unit 83 and the optical path length difference applying mechanism 90.

Although not illustrated, the configuration of the present embodiment may be combined with the configuration of the first embodiment and the configuration of the second embodiment. Specifically, the speckle reduction unit 80 may include the oscillating unit 81, the driving current superimposing unit 83, and the optical path length difference applying mechanism 90.

As described above, the speckle reduction unit 80 may include a plurality of the same or different means.

In this case, speckle can be more effectively reduced by providing the speckle reduction units 80 having mutually different principles, that is, the driving current superimposing unit 83 and the optical path length difference applying mechanism 90.

[Others]

For the mechanism similar to the optical path length difference applying mechanism 90 of the present embodiment, the phase multiplexing unit 80a that is difficult to switch between driving and stopping in itself may be disposed in the position of the optical path length difference applying unit 97. An example of the phase coupler 80a that is difficult to switch between driving and stopping is a mode scrambler of various types obtained by adding a bending portion to a light guide member. Multiplexing the phase by the mode scrambler averages the speckle in the observed portion image, and consequently reduces the speckle.

It suffices that each of the reflecting members 93a and 93b includes an optical member, such as an optical switch, that can vary the traveling direction of the laser light in accordance with the control of the controller 14, that is, the observation mode.

The optical path length difference controller 99 may change optical characteristics of the reflecting members 93a and 93b, to cause the reflecting members 93a and 93b to reflect or transmit the laser light, in accordance with the control of the controller 14, that is, the observation mode.

The optical path length difference applying unit 97 may divide the laser light into a plurality of luminous fluxes using an optical member such as a mirror, provide the luminous fluxes with mutually different optical path lengths, and couple the divided luminous fluxes into a luminous flux again.

Fourth Embodiment

[Configuration]

Figure 4:
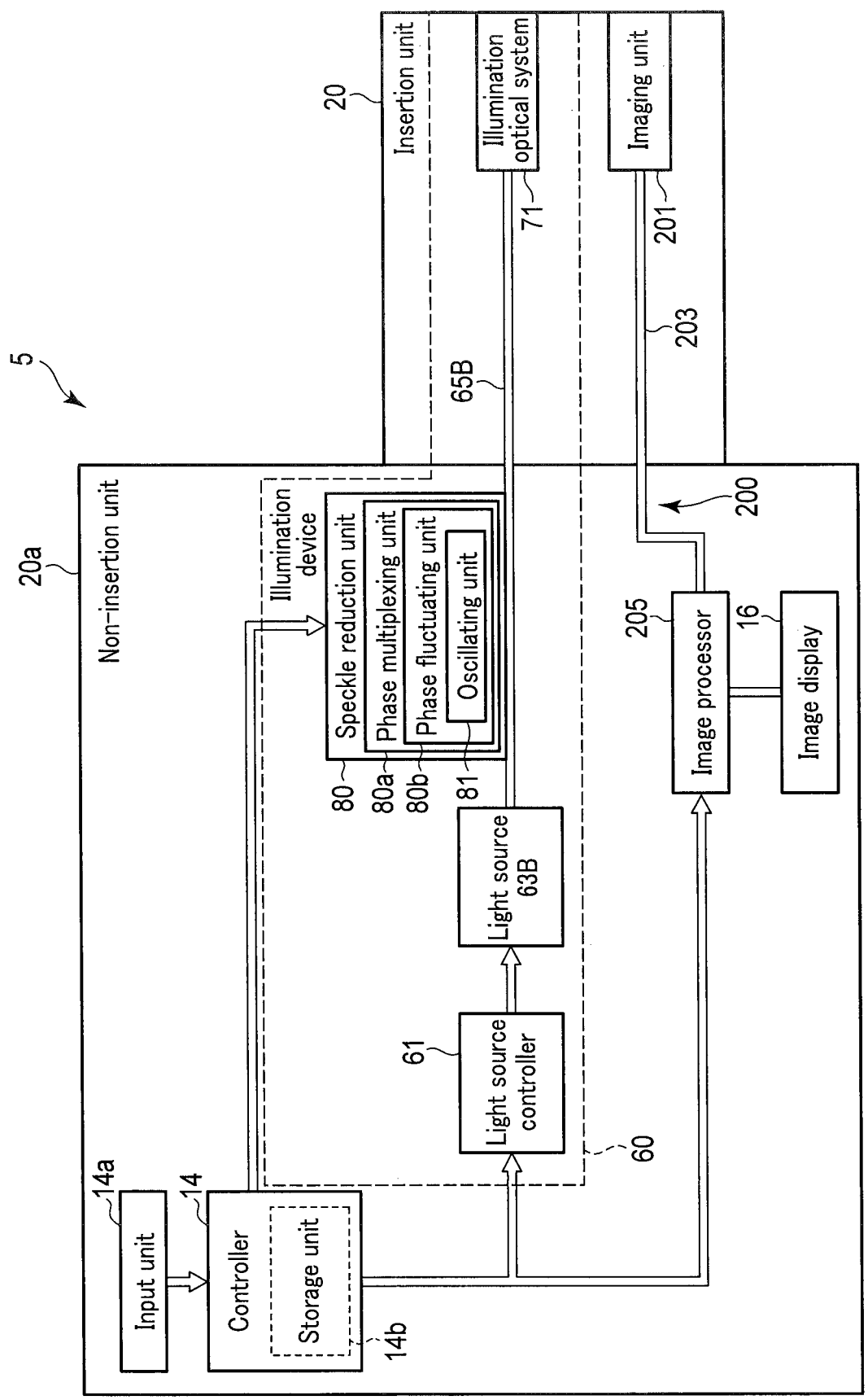
FIG. 4 is a schematic diagram of an endoscopic system according to a fourth embodiment.

The following is an explanation of only points different from the first embodiment, with reference to FIG. 4.

In the present embodiment, the observation modes include, for example, the white-light observation mode and the speckle observation mode.

[Illumination Device 60]

An illumination device 60 includes a light source controller 61, a light source 63B, a light guide member 65B, and an illumination optical system 71.

The light guide member 65B is optically connected to the light source 63B and the illumination optical system 71, and guides the light emitted from the light source 63B to the illumination optical system 71.

The illumination optical system 71 includes, for example, fluorescent substance. The fluorescent substance has a property of being excited by blue laser light, and emitting yellow fluorescent light. For this reason, the illumination optical system 71 emits white light generated by combing yellow fluorescent light emitted from the fluorescent substance and blue laser light transmitted through the fluorescent substance.

[Effects]

The following is an explanation of functions in the white-light observation mode and the speckle observation mode, and only points different from the first embodiment will be explained.

[White-Light Observation Mode]

In the white-light observation mode, the controller 14 controls the light source controller 61 such that the light source 63B is driven to be turned on. Based on the control of the controller 14, the light source controller 61 controls the light source 63B such that the light source 63B is driven to be turned on. Thereby, the light source 63B emits blue laser light, and the blue laser light is guided to the illumination optical system 71 by the light guide member 65B.

In the white-light observation mode, the controller 14 controls the speckle reduction unit 80 such that the speckle reduction unit 80 is driven.

Accordingly, when the blue laser light is guided to the illumination optical system 71 by the light guide member 65B, the oscillating unit 81 of the speckle reduction unit 80 oscillates the light guide member 65B. For this reason, the phase of the blue laser light temporally fluctuates. Specifically, in the blue laser light, a plurality of blue laser lights having mutually different phases are guided in a temporally different state.

In the phase-fluctuated blue laser light, part of the blue laser light is converted into yellow fluorescent light by the fluorescent substance, and the other part of the blue laser light is transmitted through the fluorescent substance. The yellow fluorescent light and the blue laser light are combined, emitted as white light from the illumination optical system 71, and applied to the observed portion. In the white light, a plurality of laser lights having mutually different phases are applied in a temporally different state to the observed portion. Accordingly, the speckle generated in the observed portion is also temporally different. The temporal difference means that the speckle differs at time intervals corresponding to the fluctuation frequency at which the oscillating unit 81 oscillates the light guide member 65B. This averages the speckle, and consequently reduces the speckle.

The imaging unit 201 images the light reflected from the observed portion as an image. The image is transmitted to the image processor 205 through the imaging cable 203. The image processor 205 performs image processing, such that an image obtained with white light has a natural shade, to generate the observed portion image. The image display 16 displays the image.

The frame rate serving as an interval at which the image processor 205 acquires an image is several fractions or more slower than the fluctuation frequency at which the oscillating unit 81 oscillates the light guide member 65B. Accordingly, in the generated observed portion image, the different speckles generated in the frame rate are averaged, and the speckle is reduced.

[Speckle Observation Mode]

In the speckle observation mode, the controller 14 controls the light source controller 61 such that the light source 63B is driven to be turned on. Based on the control of the controller 14, the light source controller 61 controls the light source 63B such that the light source 63B is driven to be turned on. Thereby, the light source 63B emits blue laser light, and the blue laser light is guided to the illumination optical system 71 by the light guide member 65B.

In the speckle observation mode, the controller 14 controls the speckle reduction unit 80 such that the speckle reduction unit 80 is stopped.

Accordingly, in the blue laser light, part of the blue laser light is converted into yellow fluorescent light by the fluorescent substance, and the other part of the blue laser light is transmitted through the fluorescent substance. The yellow fluorescent light and the blue laser light are combined, emitted as white light from the illumination optical system 71, and applied to the observed portion. Because the oscillating unit 81 of the speckle reduction unit 80 does not act on the blue laser light, speckle occurs in the observed portion irradiated with the blue laser light.

The imaging unit 201 images the light reflected from the observed portion as an image. The image is transmitted to the image processor 205 through the imaging cable 203. The image processor 205 performs image processing, such that the state of the observed portion is analyzed with the speckle, to generate the observed portion image. The image display 16 displays the image.

[Effects]

In present embodiment, the configuration can be simple.

[Modification]

For speckle observation, a light source that emits light for speckle observation may be disposed. In this case, the light coupler 67 is disposed to couple the light emitted from the light source and the blue laser light emitted from the light source 63B. The light emitted from the light source has a property of not being wavelength-converted by the fluorescent substance but transmitted through the fluorescent substance.

The present invention is not limited to the above embodiments, but can be carried out with modified constituent elements within a range not departing from the gist thereof. Various inventions can be formed of appropriate combinations of the plurality of constituent elements disclosed in the above embodiments.

What is claimed is:

1. An endoscopic system for observing an observed portion, the endoscopic system comprising:
   a speckle reduction unit configured to be controlled to reduce speckle generated on the observed portion by light that has coherence, where the light that has coherence is emitted by an illumination device;
   an image sensor configured to capture images of the observed portion; and
   a controller comprising hardware, wherein the controller is configured to:
     receive one of a selection signal indicating a non-speckle observation mode and a selection signal indicating a speckle observation mode;
     in response to receiving the selection signal indicating the non-speckle observation mode:
       control the illumination device to emit the light that has coherence corresponding to the non-speckle observation mode;
       control the speckle reduction unit to reduce speckle generated on the observed portion by the light that has coherence; and
       control the image sensor to capture images of the observed portion in conjunction with reduced speckle generated; and
     in response to receiving the selection signal indicating the speckle observation mode:
       control the illumination device to emit the light that has coherence corresponding to the speckle observation mode;
       control the speckle reduction unit to not reduce speckle generated on the observed portion by the light that has coherence; and
       control the image sensor to capture images of the observed portion in conjunction with the speckle generated as the observed portion is irradiated with the light that has coherence.

2. The endoscopic system according to claim 1, further comprising:
   an insertion unit configured to be inserted into a desired region to approach the observed portion; and
   an illumination optical system configured to emit the light emitted by the illumination device to the observed portion,
   wherein the illumination optical system is incorporated in the insertion unit.

3. The endoscopic system according to claim 2,
wherein the illumination device comprises:
- a light source configured to emit light in accordance with the non-speckle observation mode and the speckle observation mode; and
- a light guide that is optically connected with the light source and the illumination optical system to guide the light emitted from the light source to the illumination optical system.

4. The endoscopic system according to claim 3,
wherein the speckle reduction unit comprises a phase multiplexing unit configured to couple a phase by converting part of the light emitted by the illumination device and generating light having a phase different from the original phase.

5. The endoscopic system according to claim 4,
wherein the phase multiplexing unit comprises a phase fluctuating unit configured to temporally fluctuate the phase of the light emitted by the illumination device such that a plurality of the lights having mutually different phases are generated in phases that are temporally different.

6. The endoscopic system according to claim 5,
wherein a speed of a period with which the phase fluctuating unit temporally fluctuates the phase of the light is faster than a frame rate of the image sensor.

7. The endoscopic system according to claim 6,
wherein the phase fluctuating unit includes an oscillator configured to oscillate the light guide such that the phase of the light emitted by the light source temporally fluctuates.

8. The endoscopic system according to claim 6,
wherein the phase fluctuating unit comprises a driving current superimposing unit configured to periodically change a driving current for the light source in a range in which the phase of the light emitted by the light source changes, such that the phase of the light emitted by the light source temporally fluctuates.

9. The endoscopic system according to claim 1,
wherein the speckle reduction unit includes an optical path length difference applying mechanism configured to apply an optical path length difference to the light emitted by the illumination device.

10. The endoscopic system according to claim 1, further comprising the illumination device, wherein the illumination device comprises:
- a light source configured to emit lights that are optically different; and
- a light coupler configured to couple the lights that are optically different into the light emitted from the illumination device toward the observed portion.

11. The endoscopic system according to claim 10,
wherein a light that is emitted by the light source in the speckle observation mode is emitted by the light source for the non-speckle observation mode.

12. The endoscopic system according to claim 10,
wherein the controller is configured to, in response to receiving the selection signal indicating the non-speckle observation mode:
- control the light source to emit at least a first light and a second light that are optically different, wherein the first light and the second light are combined by the light coupler and emitted as white light;
- control the speckle reduction unit to reduce speckle generated on the observed portion by the white light; and
- control the image sensor to capture images of the observed portion in conjunction with reduced speckle generated.

* * * * *